US00PP27591P2

(12) United States Plant Patent
Udagawa

(10) Patent No.: US PP27,591 P2
(45) Date of Patent: Jan. 24, 2017

(54) ***CLEMATIS* PLANT NAMED 'TAIGA'**

(50) Latin Name: ***Clematis* hybrid**
Varietal Denomination: Taiga

(71) Applicant: Koichiro Ochiai, Fujisawa (JP)

(72) Inventor: Masatake Udagawa

(73) Assignee: Koichiro Ochiai, Kanagawa (JP)

( * ) Notice: Subject to any disclaimer, the term of this patent is extended or adjusted under 35 U.S.C. 154(b) by 131 days.

(21) Appl. No.: 14/544,543

(22) Filed: Jan. 20, 2015

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Keith Robinson
(74) *Attorney, Agent, or Firm* — Penny J. Aguirre

(57) ABSTRACT

A new cultivar of hybrid *Clematis*, 'Taiga', characterized by its large, double flowers, its purple flowers with the tips of the outer tepaloids uniquely colored light yellow-green with center tepaloids light yellow-green, and its sterile flowers with no reproductive organs present.

2 Drawing Sheets

Botanical classification: *Clematis* hybrid.
Variety denomination: 'Taiga'.

BACKGROUND OF THE INVENTION

The present invention relates to a new and distinct cultivar of *Clematis*, botanically of hybrid origin, and will be referred to hereafter by its cultivar name 'Taiga'. 'Taiga' is grown as an herbaceous perennial for landscape use or as a terrace pot plant.

'Taiga' was derived from a breeding program conducted by the Inventor in Tokyo, Japan. The Inventor, now deceased, made years of crosses between plants of *Clematis florida* (and other species now included in the Florida group of *Clematis*) and plants of *Clematis integrifolia*, and proprietary hybrids between them. The parental plants were unnamed and unpatented, however the Inventor's records could not be found for detailed information in regards to the parents. 'Taiga' was selected by the Inventor as a single unique plant from a batch of seedlings in 2000.

Asexual propagation of the new cultivar was first accomplished by internodial stem cuttings by the Inventor in Tokyo, Japan in 2000. Asexual propagation by internodial stem cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors. These attributes in combination distinguish 'Taiga' as a unique cultivar of *Clematis*.

1. 'Taiga' exhibits large, double flowers.
2. 'Taiga' exhibits purple flowers with the tips of the outer tepaloids uniquely colored light yellow-green with center tepaloids light yellow-green.
3. 'Taiga' exhibits sterile flowers with no reproductive organs present.

'Taiga' can be most closely compared to the *Clematis* cultivars 'Vyvyan Pennell' (not patented) and 'Multi Blue' (not patented). Both are similar to 'Taiga' in having large double purple flowers. 'Vyvyan Pennell' differs from 'Taiga' in having petaloids that lack light yellow-green tips and are tinged rose in color and in having some reproductive organs. 'Multi Blue' differs in having tepaloids that are tinged with silver.

BRIEF DESCRIPTION OF THE DRAWINGS

The accompanying colored photographs illustrate the overall appearance and distinct characteristics of the new *Clematis*. The photographs were taken of a two year-old plant of the new cultivar as grown in a greenhouse in a 17-cm container in Aalsmeer, The Netherlands.

The photograph in FIG. 1 provides a side view of 'Taiga' in bloom.

Figure 1:
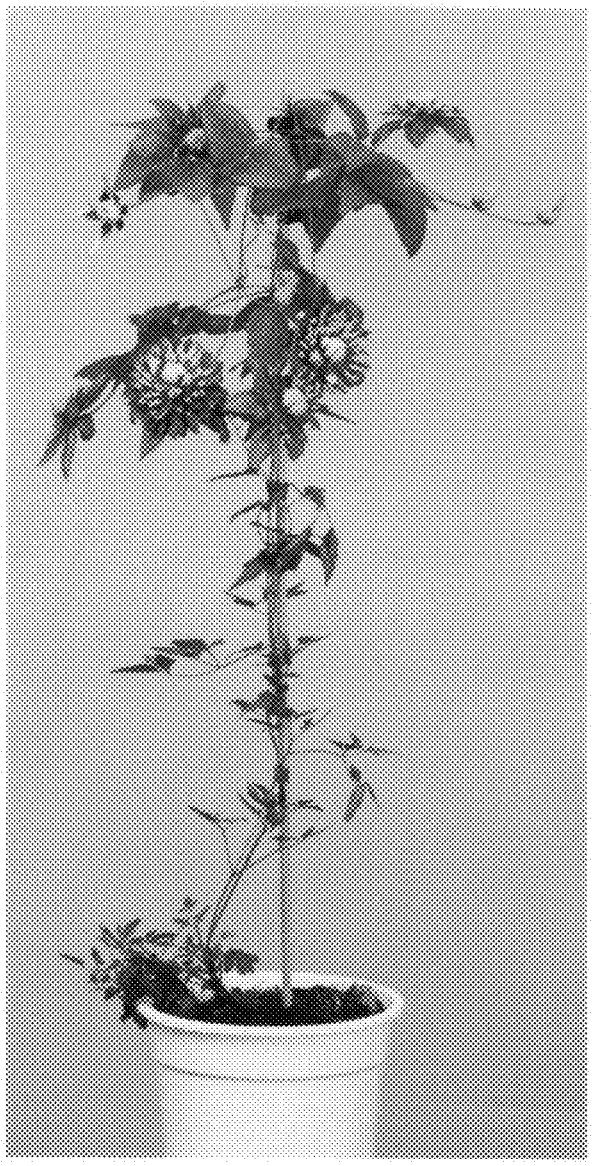
Figure 2:
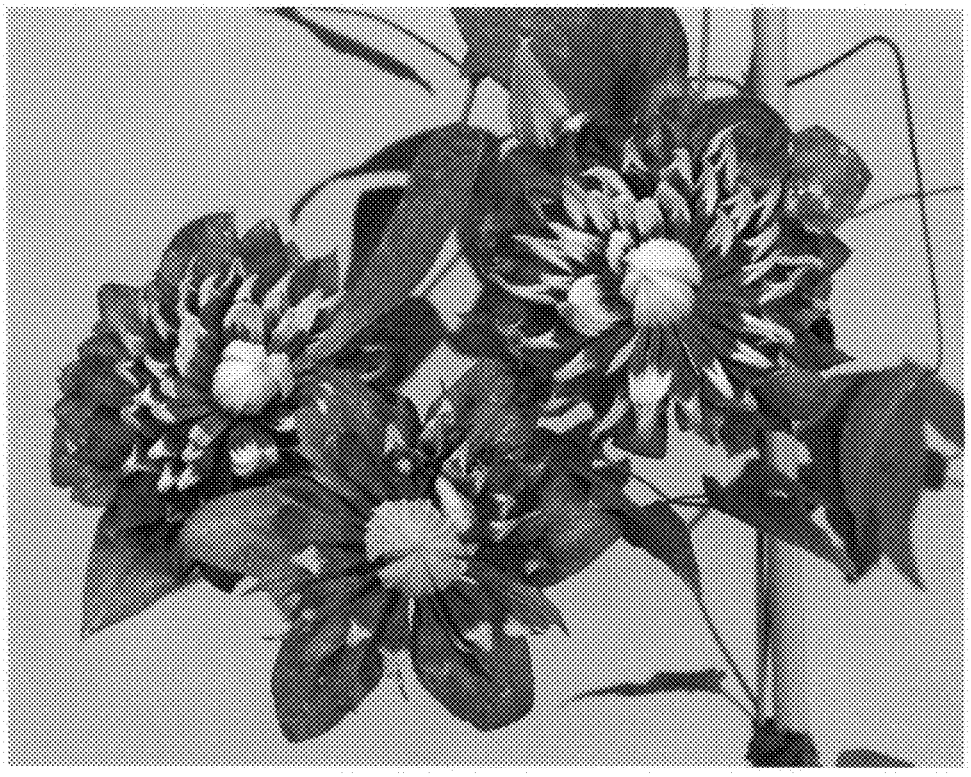
FIG. 2 provides a close-up view of the inflorescences of 'Taiga'.
Figure 3:
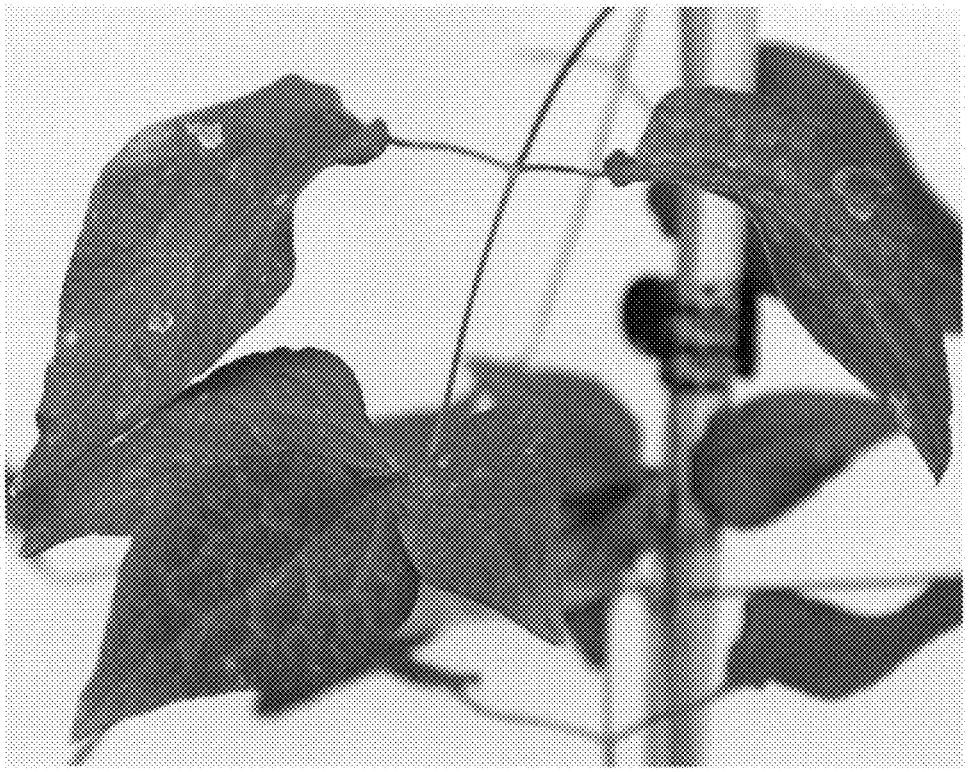
FIG. 3 provides a close-up view of the foliage of 'Taiga'.

The colors in the photographs are as close as possible with the digital photography and printing techniques utilized and the color codes in the detailed botanical description accurately describe the new *Clematis*.

DETAILED BOTANICAL DESCRIPTION

The following is a detailed description of two year-old plants of 'Taiga' as grown in a greenhouse in 17-cm containers in Aalsmeer, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms in May through June in The Netherlands.

*Plant type.*—Deciduous perennial vine.

*Plant habit*.—Climbing with stems emerging from base.

*Height and spread*.—An average of 80 cm in height and 30 cm in width.

*Cold hardiness*.—At least in U.S.D.A. Zone 6.

*Diseases and pests*.—No susceptible or resistance to pests and diseases has been observed.

*Root description*.—Fleshy, fibrous, and fine, about 158D in color.

*Growth rate*.—Moderate, an average of 10 cm per month in spring.

*Propagation*.—Internodial soft wood cuttings from vegetative shoots.

*Root initiation*.—Roots develop in 6 weeks in summer under greenhouse conditions.

*Time required for root development*.—75 to 90 days to develop a 5-cm container from a 5-cm cutting.

Stem description:

*Shape*.—Round.

*Stem color*.—Young stems 146C, mature stems N199C to N199D.

*Stem size*.—Average of 77 cm in length and 1.75 cm in diameter.

*Stem surface*.—Slightly glossy, young stems are moderately pubescent with short adpressed hairs an average of 0.5 mm in length and 157D in color, mature stems smooth.

*Stem aspect*.—Climbing.

*Stem strength*.—Flexible and strong.

*Stem quantity*.—Average of 2 basal branches in a 17-cm container.

Foliage description:

*Leaf arrangement*.—Opposite.

*Leaf division*.—Primarily ternate, occasionally single.

*Internode length*.—Up to 9.9 cm.

*Leaf size*.—Up to 4.7 cm in length and 9 cm in width.

*Leaf quantity*.—Average of 16 (8 pairs) per branch.

*Leaf shape*.—Trifoliate, ovate in outline.

*Leaf fragrance*.—None.

*Leaf attachment*.—Petiolate with leaflets petiolulate.

*Leaf surface*.—Both surfaces are glabrous and very slightly glossy.

*Leaf size*.—Average of 6 cm in length and 9 cm in width.

*Leaf color*.—Young upper surface; between 143B and 144A, young lower surface; between 143C and 144A, mature upper surface; 137B, mature lower surface; between 138B and 147B.

*Leaflet shape*.—Ovate to trifoliate.

*Leaflet venation*.—Pinnate, upper surface color 146D, lower surface color 146C.

*Leaflet margin*.—Entire, slightly undulate.

*Leaflet size*.—Average of 4.7 cm in length and 3.8 cm in width.

*Leaflet quantity*.—Average of 3 per leaf.

*Leaflet apex*.—Acute.

*Leaflet base*.—Cuneate.

*Petioles*.—Average of 5.3 cm in length, 1 mm in diameter, color is 146B, surface is glabrous.

*Petiolulates*.—Average of 2 nun in length, 1 mm in diameter, color is 146B, surface is glabrous.

Inflorescence description:

*Inflorescence type*.—Solitary flowers, double with early spring flowers sometimes single (single flowers reported but not observed on plants for data collection).

*Flowering habit*.—Blooms on previous year's growth.

*Flower arrangement*.—Terminal in spring, terminal and axillary in summer.

*Peduncles*.—Average of 10.7 cm in length and 1 mm in diameter, pedicels of terminal flowers straight on top of main stems, pedicels of axillary flowers in an average angle of 50° to main stem, moderately strong and 144B in color, surface glabrous.

*Flower bud description*.—Average of 3 cm in length and 1.7 cm in diameter, ovate in shape, 145A to 145B in color, base tinged 93B to 93C in color.

*Flower fragrance*.—None.

*Lastingness of the flowers*.—Individual flowers last about 10 days.

*Flower quantity*.—Average of 3 flowers per lateral stem.

*Flower type*.—Fully double, rotate.

*Flower aspect*.—Outward to upright.

*Flower size*.—Average of 5 cm in depth and 9.6 cm in diameter.

*Petals*.—No petals present.

*Sepals*.—No sepals present.

*Tepals*.—Upper surface texture glabrous, matte and velvety, lower surface texture matte and moderately covered with soft short hairs; average of 0.5 mm in length and too small to measure color, rotate in arrangement, average of 6 and un-fused, elliptic to obovate in shape, entire margins, acute apex, base truncate, average of 5.3 cm in length and 2.4 cm in width, color: when opening upper surface; 79C, base N88A to N88B, when opening lower surface; N88C to N88D with 145C to 145D in the center forming a band, fully opened upper surface; 90B to 90C, base 90A, fully opened lower surface; 92B, 157A to 157B in the center forming a band, fading both surfaces; 86B, base N89B.

*Tepaloids*.—Upper and lower surfaces are very slightly glossy, arrangement is rotate, in multiple rows forming fully double flowers, average of 210, narrow obovate to oblanceolate in shape, entire margins, base truncate, average of 3 cm in length; varying between 3.8 (outer tepaloids) and 8 mm (inner tepaloids), average of 8 mm in width; varying between 1.2 cm (outer tepaloids) and 2 mm (inner tepaloids), color: immature and mature both surfaces 86B to 86C, upper 50% to 30% is 154D with both surfaces of center tepaloids 154D, fading both surfaces; N87A, base N88B.

Reproductive organs:

*Reproductive organs*.—Flowers are fully double with no reproductive organs present and are fully sterile.

*Seed and fruit*.—No seed or fruit.

It is claimed:

1. A new and distinct cultivar of *Clematis* plant named 'Taiga' as herein illustrated and described.

* * * * *